US00PP10673P

United States Patent [19]

Olesen et al.

[11] Patent Number: Plant 10,673

[45] Date of Patent: Nov. 10, 1998

[54] MINIATURE ROSE PLANT NAMED 'POULROAR'

[76] Inventors: L. Pernille Olesen; Mogens N. Olesen, both of Hillerødvejen 49, DK-3480, Fredensborg, Denmark

[21] Appl. No.: 846,373

[22] Filed: Apr. 30, 1997

[51] Int. Cl.[6] ..... A01H 5/00

[52] U.S. Cl. ..... Plt./10.1

[58] Field of Search ..... Plt./10, 10.1

[56] References Cited

PUBLICATIONS

UPOV–ROM, Apr. 1997, Plant Variety Database, GTI Jouve Retrieval Software, Citations for 'Poulroar'.

*Primary Examiner*—Howard J. Locker

[57] ABSTRACT

A new orange colored miniature rose plant which has non-fading orange flowers and excellent keepability. The variety successfully propagates from softwood cuttings and is suitable for year round production in commercial glasshouses. This new and distinct variety has shown to be uniform and stable in the resulting generations from such asexual propagation.

2 Drawing Sheets

SUMMARY OF THE DISCOVERY

The present invention constitutes a new and distinct variety of miniature rose plant which was discovered in a cultivated area. The naturally occurring mutation of unknown causation was discovered on a branch of POULoral in a controlled planting, a patented variety described and illustrated in U.S. Plant Pat. No. 9,018 and issued on Dec. 20, 1994. The new variety is named 'POULroar'.

The rose plant of the present discovery has a unique combination of characteristics which are outstanding in the new variety and which distinguish it from the original rose 'POULoral' as well as all other varieties which we are aware of. For example, the new variety has:

1. Uniform orange colored flowers with excellent keepability;
2. Attractive long lasting foliage and compact growth,
3. Year-round flowering under glasshouse conditions;
4. Suitability for production from softwood cuttings in pots;
5. Durable flowers and foliage which make the variety suitable for distribution in the floral industry.

This combination of qualities was lacking in miniature pot rose varieties that were in commercial cultivation and the qualities have been substantially achieved in the new variety.

The resulting mutation was planted in a controlled environment and evaluations were conducted of the resulting rose plants. 'POULroar' was selected by L. Pernille and Mogens N. Olesen in their rose development program in Fredensborg, Denmark in Spring of 1993.

Asexual reproduction of 'POULroar' by cuttings and traditional budding was first done by L. Pernille and Mogens N. Olesen in August of 1993. This initial and subsequent propagations have demonstrated that the characteristics of 'POULroar' are true to type and are transmitted from one generation to the next.

BRIEF DESCRIPTION OF THE DRAWING

Sheet 1 of the accompanying color illustrations shows as true as is reasonably possible to obtain in color photographs of this type, the typical characteristics of the buds, flowers, leaves, and stems of 'POULroar'.

Sheet 2 shows 'POULroar' as a potted plant.

Specifically illustrated in Sheet 1:

1. Stem or entire plant showing branching and the attachment of leaves, buds, and peduncles;
2. Flower bud, partially opened bud, and open bloom;
3. Flower petals, detached;
4. Sepals, receptacle, and peduncle;
5. Flowering stem as well as a bare stem exhibiting thorns;
6. Leaves.

DETAILED DESCRIPTION OF THE VARIETY

The following is a detailed description of 'POULroar', as observed in its growth in glasshouses in Fredensborg, Denmark and Half Moon Bay, Calif. and in field nursery in Applegate, Oreg. Descriptions were made from plants treated with growth regulators normally used in the greenhouse production process. The growth regulator Paclobutrazol was applied at 15 ppm weekly for four weeks beginning at a plant age of 6 weeks.The peduncle lengths mentioned may actually be shorter and the foliage color several shades darker than or untreated specimens. Color references are made using The Royal Horticultural Society (London, England) Colour Chart, 1995.

For a comparison, the nearest existing rose variety is POULoral, a patented variety described and illustrated in U.S. Plant Pat. No. 9,018 and issued on Dec. 20. 1994. Chart 1details several physical characteristics of the applicant and the comparison varieties.

| Characteristic | 'POULroar' | 'POULoral' |
|---|---|---|
| Flower bud | 47C of the Red Group | 41C of the Red Group |
| Flower bloom, upper surface of petal | 40A of the Red Group | 41C of the Red Group |
| Flower bloom, reverse side of petal | 47D of the Red Group | 43C of the Red Group |

Mutation resulting from: POULoral (U.S. Plant Pat. No. 9, 018).

Classification:

*Botanical.*—*Rosa hybrida.*

*Commercial.*—Miniature.

Flower and Flower Bud

Blooming cycle: Recurrent.

Flower bud:

*Size.*—10–12 mm in length when petals are just begining to unfurl.

*Bud form.*—Initially ovoid, then globular as bud opens.

*Bud color.*—RHS 47 C of the Red Group as petals begin to unfurl.

*Sepals.*—RHS 137 C of the Green Group. Weak foliaceous appendages on two of the five sepals. Surfaces of sepals moderatiely pubescent.

*Peduncle.*—Surface. Glabrous. Length: 35–45 mm lengths. Color: RHS 138 A of the Green Group. Prickles: Absent.

*Receptacle.*—Surface: Smooth. Shape: Urn shaped. Size: Small. 5×5 mm. Color: R.H.S 146 C of the Yellow-Green Group.

*Borne.*—Generally singularly.

Flower bloom:

*Diameter.*—Small. 49 mm. average opening.

*Form.*—Upon opening, ovoid to globular. Completely open, flower form is flat.

*Petalage.*—Double. Average range: Above 40.

*Color.*—Upon opening, the upper surface is R.H.S 40 A of the Red Group. Upon opening, the reverse side is R.H.S 47 D of the Red Group. After opening, the upper surface is RHS 40 B of the Red Group. After opening, the reverse surface is R.H.S 47 D of the Red Group. A basal petal spot exists on both the inner and outer side of the petal. The petal spot is R.H.S 2 C of the Yellow Group.

*Reflex.*—Petals reflex backwards somewhat.

*Fragrance.*—Slight.

*Duration.*—Very long lasting.As a pot rose, bloom lasts from 14–18 days.

Reproductive Organs:

*Pollen.*—Limited. Yellow Group 4D.

*Anthers.*—Size: Small. Color: Yellow-Green Group 150D.

*Filaments.*—Color: Yellow-Green Group 150D.

*Stigmas.*—Location is superior to anthers.

*Styles.*—Color: Yellow-Green Group 150D.

Plant

Plant growth: Vigorous, upright, branching, dwarf. When grown as a 10 cm pot plant, the average height of the plant itself is 16–18 cm and the average width is 18–20 cm. When grown as a nursery plant on its own roots the average plant height is 30–35 cm and the average plant width is 25–30 cm.

Stems:

*Color.*—Young wood: Green Group 159 C. Older wood: Green Group 138 A.

*Thorns.*—Incidence: Few thorns. Size: Average length: 3 mm. Color: Translucent Red Group 49 C.

*Bark.*—Young wood: Smooth. Older wood: Smooth.

Plant foliage:

*Normal number of leaflets on average leaves.*—5 leaflets.

*Leaf size.*—Small. 65 mm × 40 mm.

*Abundance.*—Average.

*Color.*—Upper leaf surface: Medium dark green. R.H.S 137 A of the Green Group. Lower leaf surface: Medium green. R.H.S 146A of the Yellow-Green Group. Juvenile foliage: Green Group 137 A. Mature foliage: Medium green. R.H.S 137 B of the Yellow-Green Group.

Plant leaves and leaflets:

*Stipules.*—Present. With foliaceous appendages. 8–10 mm. Color: Green Group 137B.

*Petiole.*—Length: 15–20 mm. Underneath: Limited prickles. Color Group: Green Group 137B.

*Edge.*—Finely serrated.

*Shape.*—Leaflets are Ovate.

*Leaflets.*—Number: 5.

*Other.*—Glossy finish. Moderately thick texture.

Disease resistance: Under cultivation, variety exhibits average resistance to rust, black spot, and *Botrytis* and above average resistance to mildew.

We claim:

1. A new and distinct variety of rose plant of the miniature class, substantially as herein illustrated and described, as a distinct and novel rose variety due to its abundant flowers with good keepability, attractive long lasting foliage and compact growth, year round flowering under glasshouse conditions, suitabiliy for production from softwood cuttings in pots, durable flowers and foliage which make the variety suitable for distribution in the floral industry.

* * * * *

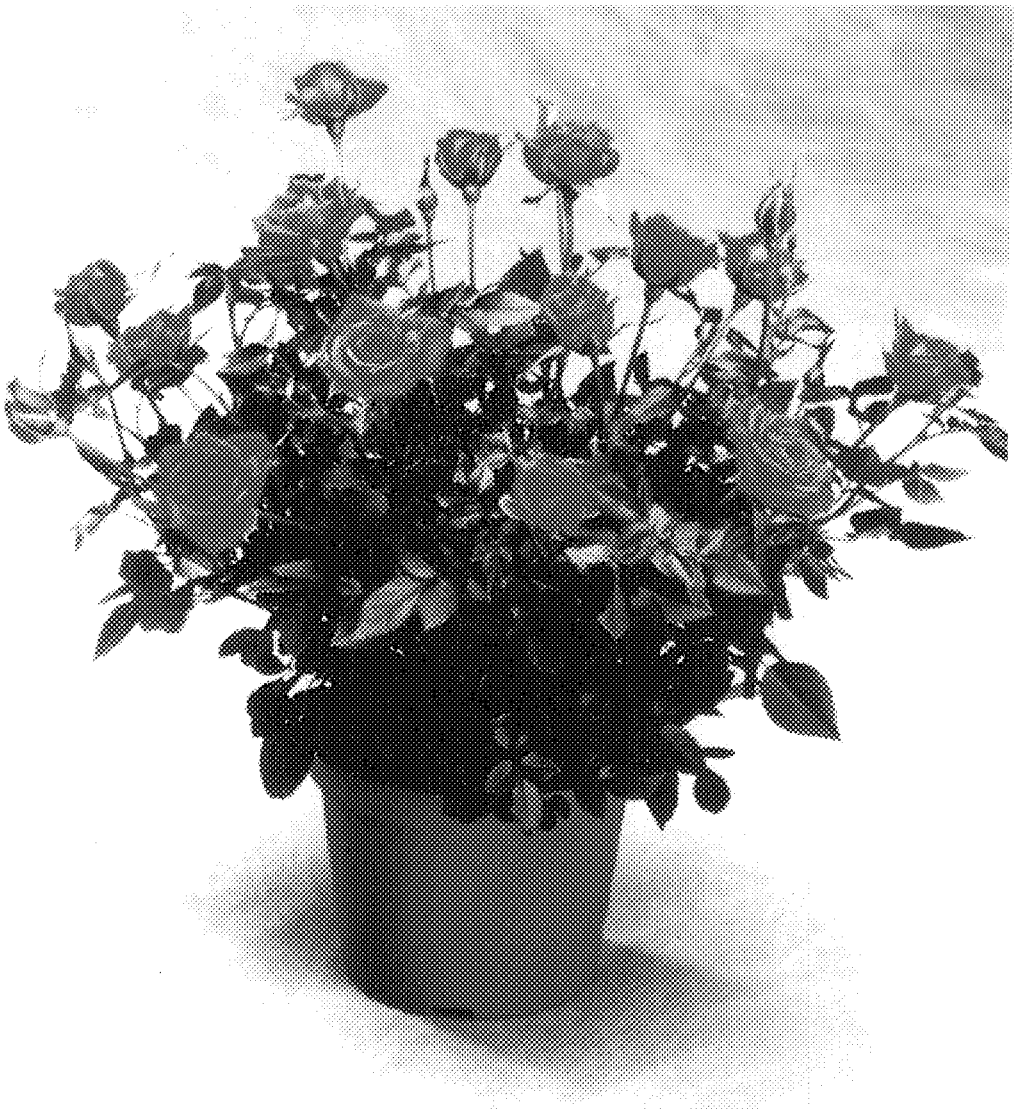

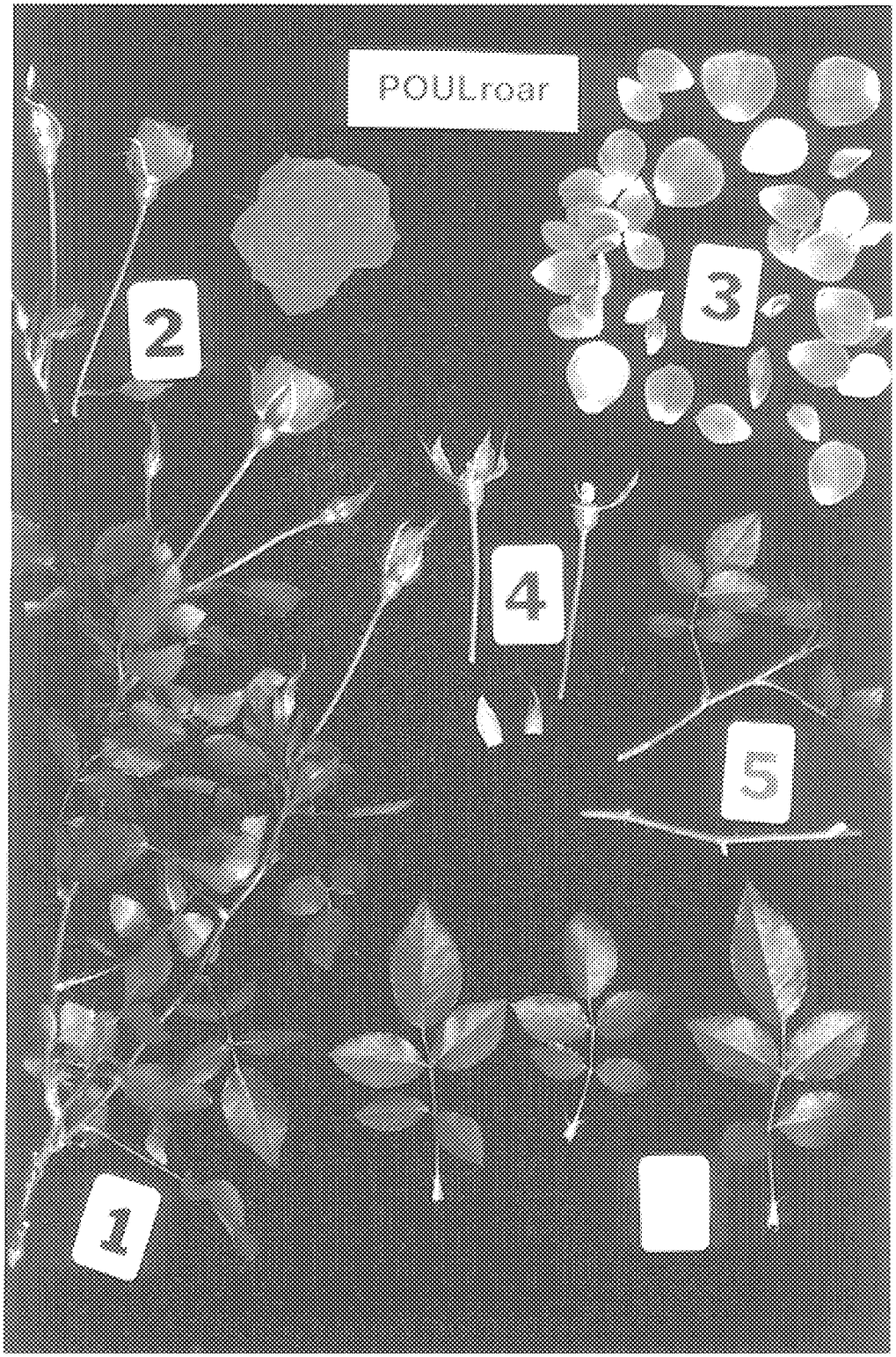
POULroar
2
3
4
5
1